(12) United States Patent
Oh et al.

(10) Patent No.: US 7,276,918 B2
(45) Date of Patent: Oct. 2, 2007

(54) SENSOR AND APPARATUS FOR MEASURING THE FLOW ELECTRIC POTENTIAL

(75) Inventors: Shin-Jong Oh, Hwaseong-si (KR);
Seung-Ho Ahn, Hwaseong-si (KR);
Hyun-Min Ahn, Hwaseong-si (KR);
Myong-Han Kim, Suwon-si (KR);
Cheol-Han Kim, Suwon-si (KR);
Sung-Moo Ryew, Suwon-si (KR)

(73) Assignee: Hyundai Motor Company, Seoul (KR)

( * ) Notice: Subject to any disclaimer, the term of this patent is extended or adjusted under 35 U.S.C. 154(b) by 106 days.

(21) Appl. No.: 11/297,834

(22) Filed: Dec. 7, 2005

(65) Prior Publication Data
US 2007/0103172 A1    May 10, 2007

(30) Foreign Application Priority Data
Nov. 1, 2005    (KR) .................... 10-2005-0103766

(51) Int. Cl.
*G01R 27/26*    (2006.01)
(52) U.S. Cl. ................... 324/671; 324/663; 324/609
(58) Field of Classification Search ............. 324/671, 324/609, 663
See application file for complete search history.

(56) References Cited

U.S. PATENT DOCUMENTS 5,093,626 A * 3/1992 Baer et al. ................. 324/671
5,386,195 A * 1/1995 Hayes et al. ............... 324/662
5,437,773 A   8/1995 Glass et al.
5,858,537 A   1/1999 Brown et al.
6,995,574 B2 * 2/2006 Sergoyan et al. .......... 324/662
6,998,854 B2 * 2/2006 Yamagishi ................. 324/658
2006/0033507 A1 * 2/2006 Gaumel et al. ............ 324/658

FOREIGN PATENT DOCUMENTS

JP    2004-279233    10/2004

* cited by examiner

*Primary Examiner*—Anjan Deb
*Assistant Examiner*—John Zhu
(74) *Attorney, Agent, or Firm*—Peter F. Corless; Edwards Angell Palmer & Dodge LLP

(57) ABSTRACT

The present invention provides a sensor and apparatus for measuring flow electric potential for evaluation of a degree of electrodeposition of paint applied to the body or chassis of a vehicle. The sensor includes a base plate part, a dielectric polymer member, a positive (+) electrode terminal and a negative (−) electrode terminal, and an insulation part. The base plate part is mounted on the outer and inner body or chassis of a vehicle, and is electrically connected to ground. The dielectric polymer member is patterned and formed on the base plate part. The positive (+) electrode terminal is connected to the dielectric polymer member and is configured to have a positive (+) polarity. The negative (−) electrode terminal is connected to the base plate part and is configured to have a negative (−) polarity. The insulation part is formed to insulate the positive (+) and negative (−) electrode terminals from each other.

11 Claims, 5 Drawing Sheets

SENSOR AND APPARATUS FOR MEASURING THE FLOW ELECTRIC POTENTIAL

CROSS-REFERENCE TO RELATED APPLICATIONS

The present application is based on, and claims priority from, Korean Application Ser. No. 10-2005-0103766, filed on Nov. 1, 2005, the disclosure of which is hereby incorporated by reference herein in its entirety.

FIELD OF THE INVENTION

The present invention relates to a sensor and apparatus for measuring flow electric potential, which enable the evaluation of the degree of electrodeposition on the body or chassis of a vehicle.

BACKGROUND OF THE INVENTION

With regard to the conventional evaluation of the degree of electrodeposition on the body or chassis of a vehicle, engineers have been directly sent to a work site in a painting line, to evaluate the degree of electrodeposition.

Accordingly, at the time of the development of vehicles, the evaluation of the degree of electrodeposition is first conducted and then following-up measures are taken, so that problems occur in that the development of vehicles is delayed, and costs increase due to the personnel expenses incurred for the engineers directly sent to the work site. Furthermore, currently, the development of a sensor for monitoring and measuring the amount of charge, that is, flow electric potential, of the body or chassis of a vehicle in the painting line in real-time at the time of the development of vehicles, is insufficient.

Therefore, the inventor of the present invention proposes the present invention in response to the necessity of a sensor for monitoring information about a painting history in real time when an electrodeposition coating process is performed.

SUMMARY OF THE INVENTION

Embodiments of the present invention provide a sensor and apparatus for measuring flow electric potential, which enable the evaluation of the degree of electrodeposition on the body or chassis of a vehicle.

A sensor for measuring flow electric potential according to the present invention includes a base plate part mounted on the outer and inner body or chassis of a vehicle, and electrically connected to ground. A dielectric polymer member is patterned and formed on the base plate part. A positive (+) electrode terminal is connected to the dielectric polymer member and is configured to have a positive (+) polarity, and a negative (−) electrode terminal is connected to the base plate part and is configured to have a negative (−) polarity. An insulation part is formed to insulate the positive (+) and negative (−) electrode terminals from each other.

BRIEF DESCRIPTION OF THE DRAWINGS

For a better understanding of the nature and object of the present invention, reference should be made to the following detailed description with the accompanying drawings, in which.

DETAILED DESCRIPTION OF THE PREFERRED EMBODIMENTS

Herein below, a preferred embodiment of the present invention will be described with reference to the accompanying drawings.

The construction of a sensor for evaluating the degree of electrodeposition of paint on the body or chassis of a vehicle (that is, the measurement of the amount of charge of paint using a sensor) according to the present embodiment is described with reference to FIG. 1.

Figure 1:
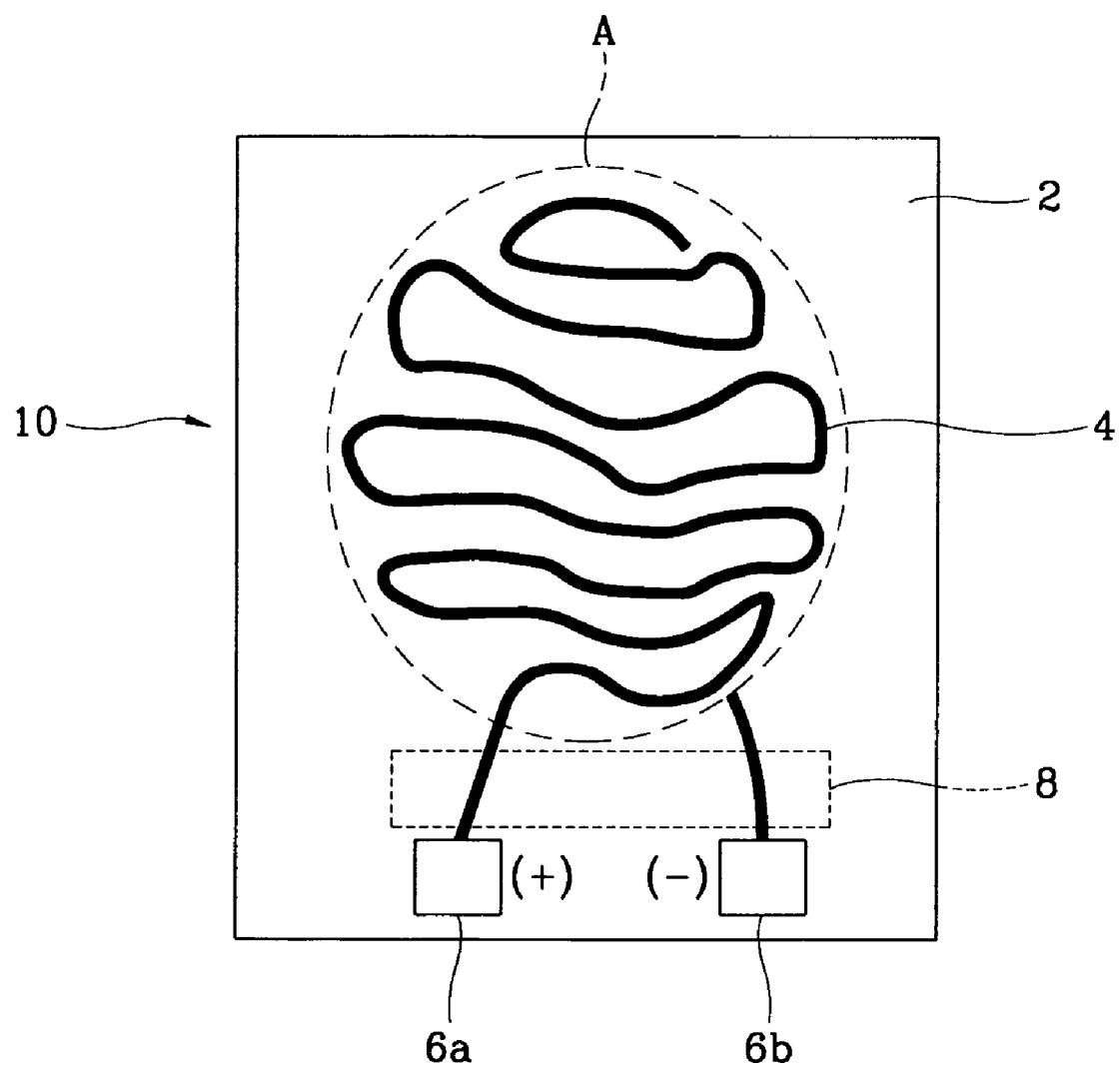
FIG. 1 is a diagram showing the construction of a sensor for measuring flow electric potential according to the present invention.

As shown in FIG. 1, the sensor 10 for measuring flow electric potential according to the present embodiment includes a base plate part 2 mounted on the outer and inner body or chassis of a vehicle and electrically connected to ground GND, a dielectric polymer member 4 patterned and formed on the base plate part 2, a positive (+) electrode terminal 6a connected to the dielectric polymer member and configured to have a positive (+) polarity, and a negative (−) electrode terminal 6b connected to the base plate part and configured to have a negative (−) polarity, and an insulation part 8 formed to insulate the positive (+) and negative (−) electrode terminals 6a and 6b from each other. For reference, in FIG. 1, reference character 'A' indicates the sensing region of the dielectric polymer member 4.

The base plate part 2 according to the present embodiment is made of a polymer material.

Furthermore, the dielectric polymer member 4 is formed to have a tentacle shape, and the sensing region A of the sensor 10 has a circular shape, thus being formed to have a wide sensing region.

Furthermore, the amount of charge of paint applied to the body and the chassis is calculated using the following Equation 1:

$$C = \frac{e_r e_0 A}{t} \quad (1)$$

where C is capacitance, t is the thickness of the dielectric polymer member,

A is the contact area of the sensor, $e_0$ is the intrinsic dielectric constant possessed by the dielectric polymer member, and $e_r$ is the dielectric constant of paint that comes into contact with the sensor.

From Equation 1, it can be appreciated that a large capacitance (or a large amount of charge) implies that paint is adhered well to the measured part of the body or chassis of the vehicle in proportion to the value of the capacitance, and the capacitance varies with the thickness and dielectric constant of the measured part of the body or chassis of the vehicle.

Figure 2:
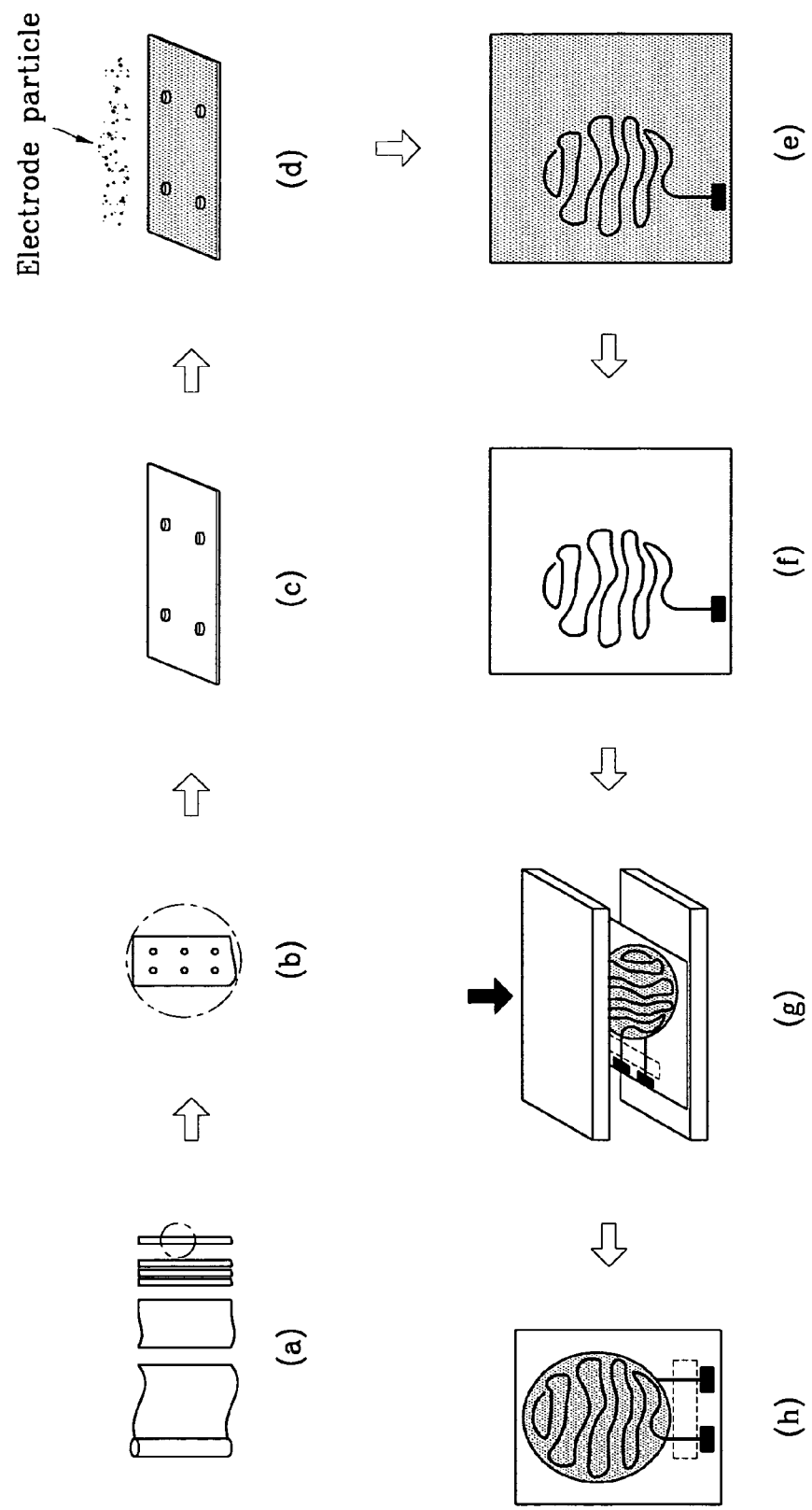
FIG. 2 is a diagram showing processes of manufacturing a sensor for measuring flow electric potential according to the present invention.

Meanwhile, the sensor is manufactured using patterning and deposition processes, which are illustrated in the manufacturing process of FIG. 2.

As shown in FIG. 2, in order to form the base plate 2, a polymer manufacturing and cutting process is performed (a) and then a process of forming holes is performed (b). Thereafter, the resulting object is plated (c), and a coating process is performed to form the electrodes (e). This process is used to form positive (+) and negative (−) electrodes. After the electrode forming process, a process of generating and exposing pattern circuitry is performed to form dielectric polymer (e). After the process (e), the manufacture of sensor is completed by etching and coverlay (protective film) hot-pressing processes (f~h).

The above-described process of manufacturing the sensor for measuring flow electric potential according to the present embodiment is similar to the commonly used process of manufacturing a polymer sensor. However, the electrode coating process according to the present embodiment differs from that of the existing process of manufacturing a polymer sensor.

Figure 3A:
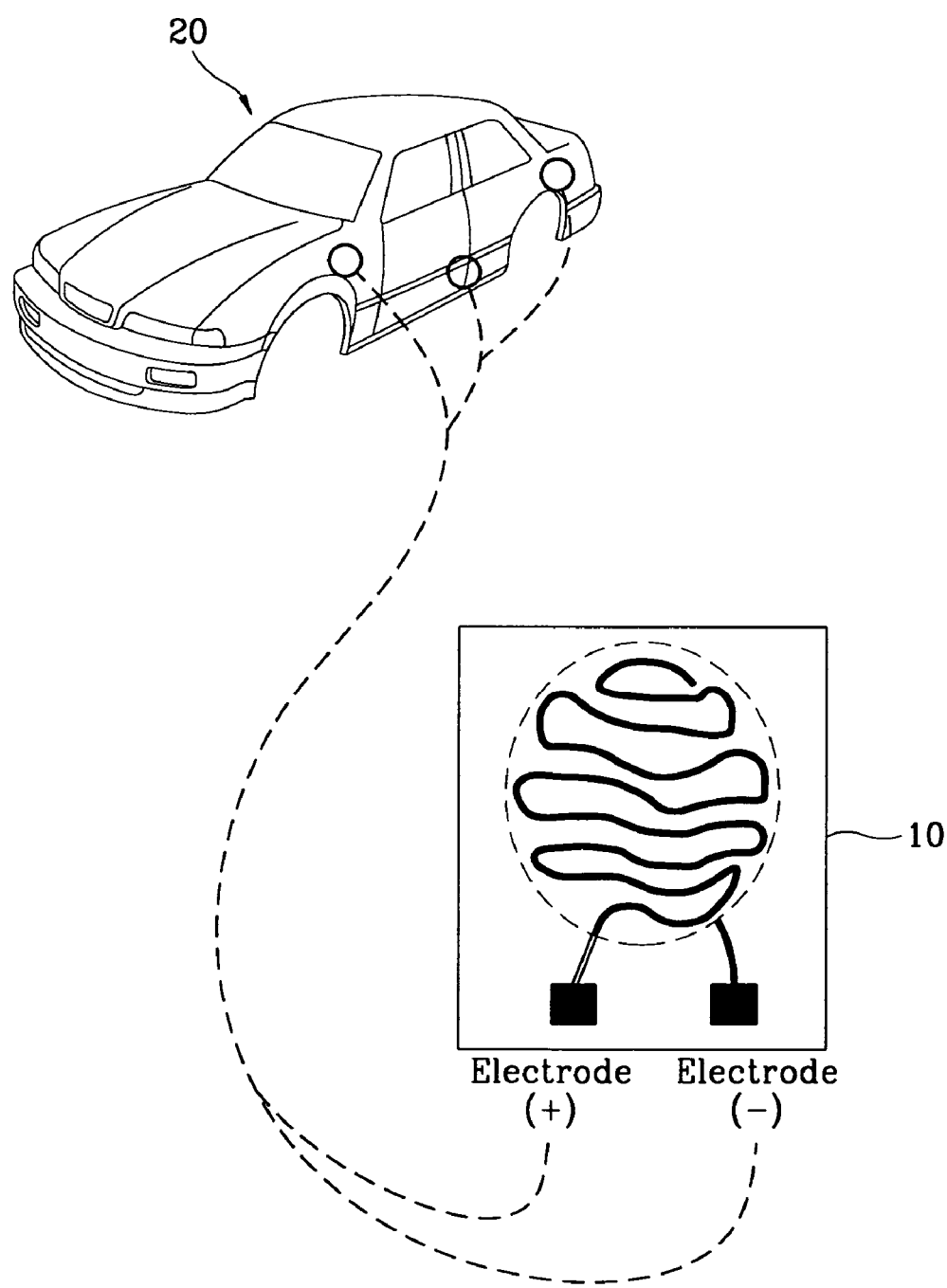
FIG. 3a is a diagram showing the measurement of the degree of electrodeposition on the body of a vehicle using the sensor according to the present invention.
Figure 3B:
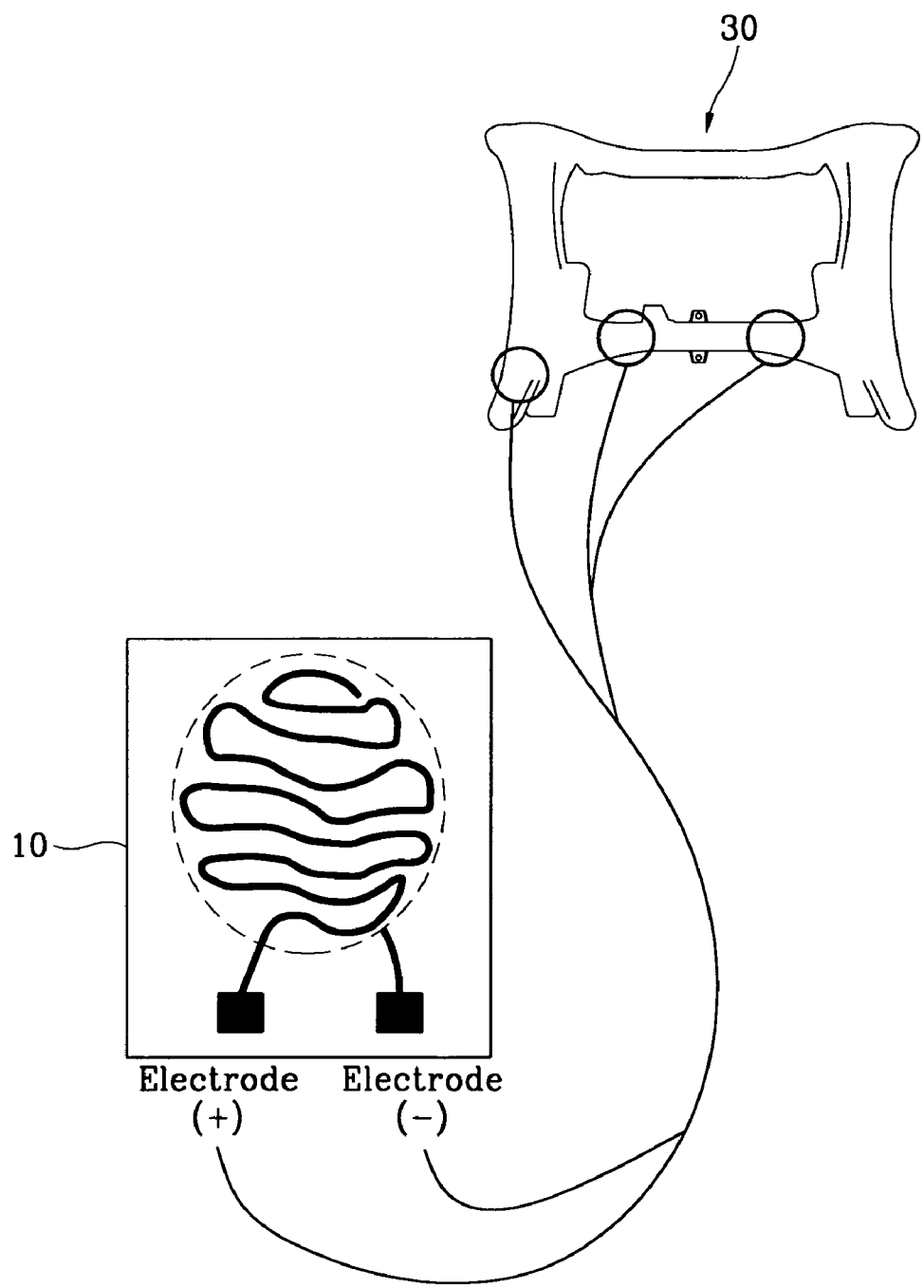
FIG. 3b is a diagram showing the measurement of the degree of electrodeposition on the chassis of a vehicle using the sensor according to the present invention.

The measurement of the degree of electrodeposition of paint applied to the body and chassis of a vehicle using the sensor according to the present embodiment is illustrated in FIGS. 3a and 3b, respectively.

As shown in FIGS. 3a and 3b, in order to measure the degree of electrodeposition of paint applied to the body 20 or chassis 30 of the vehicle, the sensor 10 is mounted on a part for measuring the degree of electrodeposition of the body 20 or chassis 30 of the vehicle and is connected to the positive (+) and negative (−) electrodes and, thereafter, flow electric potential is measured through the sensing region of the dielectric polymer member 4. Accordingly, the degree of electrodeposition can be evaluated by measuring the amount of charge of the paint.

Figure 4:
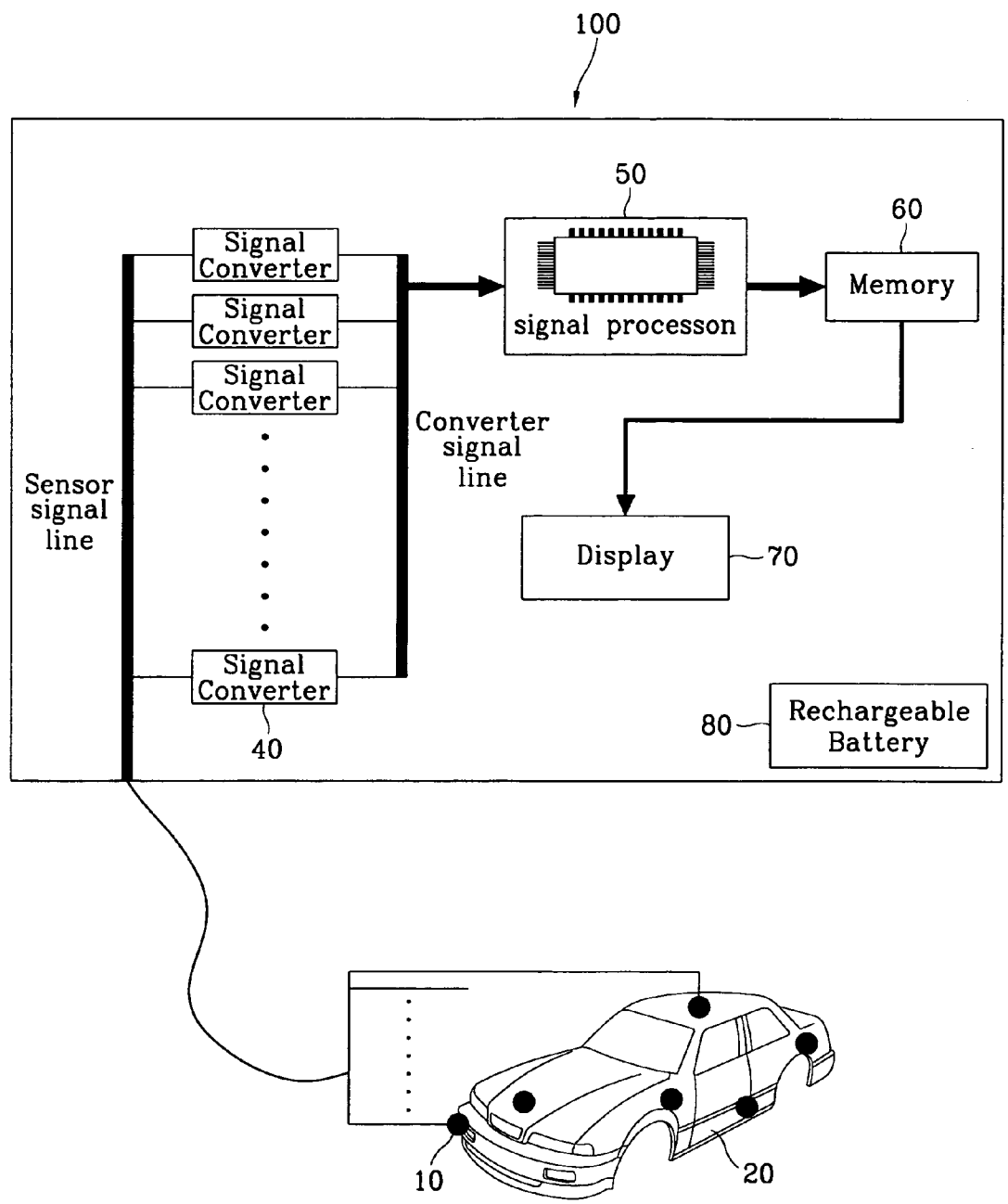
FIG. 4 is a diagram showing the construction of an apparatus for measuring flow electric potential according to the present invention.

Meanwhile, as shown in FIGS. 3a and 3b, the construction of a device for monitoring the flow electric potential, that is, the amount of charge, which is measured by each of the sensors mounted on the body and chassis of the vehicle, in real time, is as shown in FIG. 4.

As shown in FIG. 4, a device 100 for monitoring the amount of charge in real time according to the present embodiment includes Analog (A)/Digital (D) converters 40 for converting signals input through positive (+) and negative (−) electrode terminals of the sensors, a signal processor 50 for processing signals output from the A/D converters 40 and outputting data corresponding to the amount of charge measured by each sensor, memory 60 for storing the data output through the signal processor 50, and a display means 70 for displaying the data stored in the memory. The device 100 further includes a rechargeable battery means for supplying power.

The above-described monitoring device can monitor the amount of charge depending on the degree of electrodeposition of paint applied to the outer and inner body or chassis of the vehicle, which is measured using the sensor, in real time.

In the interpretation of the technical scope of the present invention, the present invention must not be interpreted as being limited only to the above-described embodiment, and the technical scope of the present invention must be defined by the logical interpretation of details described in the accompanying claims.

In a sensor for measuring flow electric potential according to the present invention, the degree of electrodeposition of paint applied to the body or chassis of a vehicle can be efficiently evaluated using a sensor for measuring flow electric potential. Furthermore, information about a painting history can be monitored using the sensor and apparatus for monitoring the amount of charge.

What is claimed is:

1. A sensor for measuring flow electric potential, the sensor having a structure for evaluation of a degree of electrodeposition of paint applied to a body or chassis of a vehicle, the sensor comprising:
   a base plate part mounted on an outer and inner body or chassis of a vehicle, and electrically connected to ground;
   a dielectric polymer member patterned and formed on the base plate part;
   a positive (+) electrode terminal connected to the dielectric polymer member and configured to have a positive (+) polarity and a negative (−) electrode terminal connected to the base plate part and configured to have a negative (−) polarity; and
   an insulation part formed to insulate the positive (+) and negative (−) electrode terminals from each other.

2. The sensor as defined in claim 1, wherein the base plate part is made of a polymer material.

3. The sensor as defined in claim 1, wherein the dielectric polymer member is manufactured to have a tentacle shape, and has a circular sensing region.

4. The sensor as defined in claim 1, wherein the sensor is manufactured using patterning and deposition processes.

5. The sensor as defined in claim 1, wherein an amount of charge of paint applied to the body and the chassis is calculated using the following Equation:

$$C = \frac{e_r e_0 A}{t}$$

where C is capacitance,
   t is a thickness of the dielectric polymer member,
   A is a contact area of the sensor,
   $e_0$ is an intrinsic dielectric constant possessed by the dielectric polymer member, and
   $e_r$ is a dielectric constant of paint that comes into contact with the sensor.

6. An apparatus for measuring flow electric potential, the apparatus comprising:
   at least one sensor set forth in claim 1; and
   a device for monitoring an amount of charge of the body or chassis of the vehicle, the device comprising at least one Analog (A)/Digital (D) converter for converting a signal input through positive (+) and negative (−) electrode terminals of the at least one sensor, a signal processor for processing signals output from the A/D converters and outputting data corresponding to an amount of charge measured by the at least one sensor, memory for storing the data output through the signal processor, and display means for displaying the data stored in the memory.

7. The apparatus as defined in claim 6, further comprising rechargeable battery means.

8. A sensor for measuring flow electric potential, the sensor having a structure for evaluation of a degree of electrodeposition of paint applied to a body or chassis of a vehicle, the sensor comprising:

a base plate part mounted on a vehicle and electrically connected to ground;

a dielectric polymer member patterned and formed on the base plate part; and a positive (+) electrode terminal connected to the dielectric polymer member and a negative (−) electrode terminal connected to the base plate part.

9. The sensor of claim 8 further comprising an insulation part formed to insulate the positive (+) and negative (−) electrode terminals from each other.

10. A vehicle assembly comprising a sensor of claim 1.

11. A vehicle assembly comprising a sensor of claim 8.

* * * * *